US012733802B2

(12) United States Patent
Solomon et al.

(10) Patent No.: US 12,733,802 B2
(45) Date of Patent: Sep. 15, 2026

(54) AIR SPECULUM

(71) Applicant: Ivy Next Ltd., Caesarea Industrial Park (IL)

(72) Inventors: Kfir Solomon, Zoran (IL); Sefi Shachrur, Pardes-Hana Karkur (IL); Gil Bachar, Tel Aviv (IL)

(73) Assignee: Ivy Next Ltd., Caesarea Industrial Park (IL)

( * ) Notice: Subject to any disclaimer, the term of this patent is extended or adjusted under 35 U.S.C. 154(b) by 502 days.

(21) Appl. No.: 18/064,267

(22) Filed: Dec. 11, 2022

(65) Prior Publication Data

US 2024/0188812 A1 Jun. 13, 2024

(51) Int. Cl.
*A61B 1/303* (2006.01)
*A61B 1/00* (2006.01)
*A61B 1/015* (2006.01)

(52) U.S. Cl.
CPC .......... *A61B 1/303* (2013.01); *A61B 1/00057* (2013.01); *A61B 1/00135* (2013.01); *A61B 1/00188* (2013.01); *A61B 1/015* (2013.01)

(58) Field of Classification Search
CPC ............ A61B 1/00091; A61B 1/00096; A61B 1/00135; A61B 1/00154; A61B 1/00188; A61B 1/015; A61B 1/018; A61B 1/126; A61B 1/303; A61B 1/32; A61B 2017/3419; A61B 2017/345; A61B 2017/3452; A61B 2017/3492; A61M 3/027; A61M 29/02; A61M 2025/1004; A61M 2039/242; A61M 3/0295; A61M 2029/025; A61M 2039/0297; A61M 2210/1067; A61M 2210/1092; A61M 2210/1475;

(Continued)

(56) References Cited

U.S. PATENT DOCUMENTS 4,681,572 A * 7/1987 Tokarz .................... A61F 5/455 600/587
8,721,534 B1 * 5/2014 Luecke ............. A61B 1/00148 600/184

(Continued)

FOREIGN PATENT DOCUMENTS

WO 2020212923 10/2020
WO WO-2020212923 A1 * 10/2020 ............. A61B 1/015
WO 2022101864 5/2022

OTHER PUBLICATIONS

Prendiville; Walter et al., Replacement Drawings for U.S. Appl. No. 16/060,871, filed Aug. 20, 2019 (Year: 2019).*
PCT/IB2023/062489 Search Report, Feb. 28, 2024.

*Primary Examiner* — Michael J Carey
*Assistant Examiner* — Stephen Floyd London
(74) *Attorney, Agent, or Firm* — AlphaPatent Associates Ltd.; Daniel J. Swirsky

(57) ABSTRACT

A speculum includes a speculum including a speculum sheath formed with one or more fluid flow lumens in fluid communication with a pump and controller unit for introducing pressurized fluid into a vagina, a pressure sensor lumen in fluid communication with the pump and controller unit for measuring fluid pressure in the vagina, and a third lumen in which is disposed a viewing device. A vaginal interface element includes flexible folds and is configured for pressing and sealing against a vagina. The vaginal interface element includes one or more pressure relief exit ports.

7 Claims, 5 Drawing Sheets

(58) Field of Classification Search

CPC .. A61M 2210/1483; A61M 2210/1491; A61M 9/0295; A61F 5/0093; A61F 5/0096; A61F 5/4405; A61F 5/442; A61F 5/445; A61F 5/455; A61F 5/4553; A61F 5/4556; A61F 2005/4415; A61F 6/16; A61H 19/34; A61H 2210/103; A61H 2009/0064; A61H 2201/013; A61H 2205/082; A61H 2205/087

USPC .......................................................... 600/119

See application file for complete search history.

(56) References Cited

U.S. PATENT DOCUMENTS

2010/0168784 A1 7/2010 Pustilnik
2011/0105850 A1* 5/2011 Voegele ............. A61B 17/3423 606/119
2011/0190595 A1* 8/2011 Bennett .................... A61B 1/05 600/300
2012/0123209 A1* 5/2012 Shibuya ............. A61B 1/00091 600/157
2015/0127016 A1* 5/2015 Sauer ................. A61B 17/4241 606/119
2015/0209073 A1* 7/2015 Ahn ................... A61B 1/00154 600/114
2015/0293877 A1* 10/2015 Liang ................. A61B 1/00016 710/33
2016/0015913 A1* 1/2016 Neuman ................ A61B 1/303 600/184
2016/0270819 A1* 9/2016 Ahluwalia ......... A61B 17/4241
2016/0287063 A1* 10/2016 Ramanujam ....... A61B 1/00087
2019/0000310 A1* 1/2019 Prendiville .............. A61B 1/32
2019/0038115 A1* 2/2019 Decherf ............. A61B 10/0291
2019/0082948 A1* 3/2019 Ford ...................... A61B 1/303
2019/0254708 A1 8/2019 Wu
2021/0022770 A1* 1/2021 Joseph ...................... A61F 6/08
2022/0000345 A1* 1/2022 Lalli .................. A61B 1/00142
2022/0296080 A1* 9/2022 Kolatt ................ A61B 1/00082
2023/0337903 A1* 10/2023 Wolny ............... A61B 1/00154
2024/0398222 A1* 12/2024 Ben-Nathan ............. A61B 1/06

* cited by examiner

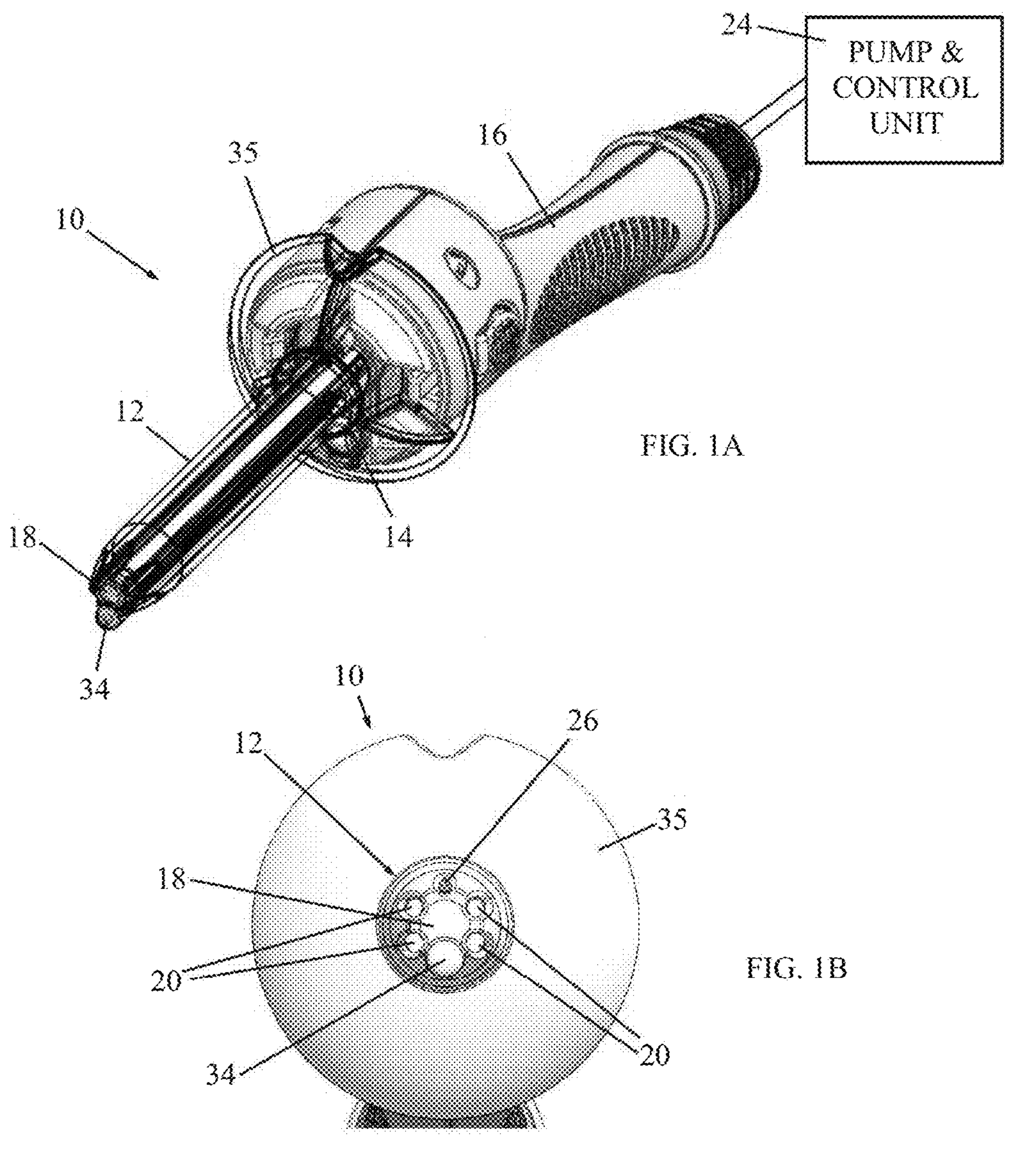
FIG. 1A
FIG. 1B
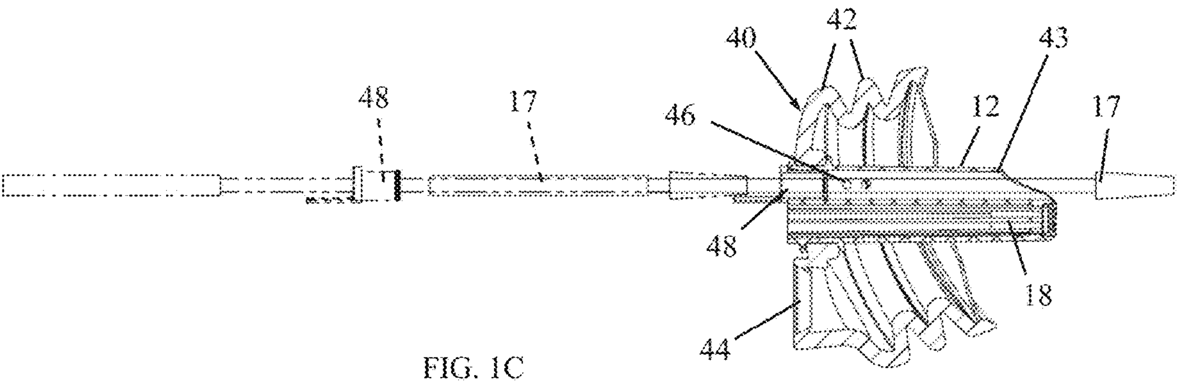
FIG. 1C

AIR SPECULUM

FIELD OF THE INVENTION

The present invention relates to vaginal speculums and particularly to a vaginal speculum that uses pressurized air to maintain a passageway through the vagina, such as to gain access to the cervix or other anatomy.

BACKGROUND OF THE INVENTION

Vaginal speculums provide access to the vagina and cervix for physical examinations and for introducing surgical instruments, such as for collecting tissue samples or for introducing medications.

Inflatable vaginal speculums have been used to examine the vagina and cervix. However, prior art inflatable speculums require sealing the septum against the vaginal walls, such as with a watertight or airtight septum or plug placed at the distal end of the speculum. The seal is meant to prevent flow of fluid (water or air) from the vagina and at the same time permit pressurized flow into the vagina.

PCT Patent Application PCT/IB2020/053647 (WO 2020/212923) describes an air speculum. The speculum includes a speculum sheath formed with a first lumen which is in fluid communication with a pump and controller unit for introducing pressurized air into a vagina. A second lumen is in fluid communication with the pump and controller unit for measuring air pressure in the vagina. A third lumen is provided for a viewing device.

PCT Patent Application PCT/IB2021/060539 (WO 2022/101864) describes another air speculum, which includes a vaginal interface element which is a soft, flexible cup with folds. The vaginal interface element may be pressed against the labia minora and/or labia majora of the vagina so as to reduce and flow of material outwards.

SUMMARY

The present invention seeks to provide an air speculum with added features to those of the air speculum described in PCT Patent Application PCT/IB2021/060539, as described in detail below.

There is thus provided in accordance with a non-limiting embodiment of the present invention a speculum including a speculum sheath formed with one or more fluid flow lumens in fluid communication with a pump and controller unit for introducing pressurized fluid into a vagina, a pressure sensor lumen in fluid communication with the pump and controller unit for measuring fluid pressure in the vagina, and a third lumen in which is disposed a viewing device, and a vaginal interface element that includes flexible folds and is configured for pressing and sealing against a vagina, wherein the vaginal interface element includes one or more pressure relief exit ports.

There is thus provided in accordance with a non-limiting embodiment of the present invention a speculum including a speculum sheath formed with one or more fluid flow lumens in fluid communication with a pump and controller unit for introducing pressurized fluid into a vagina, a pressure sensor lumen in fluid communication with the pump and controller unit for measuring fluid pressure in the vagina, and a third lumen in which is disposed a viewing device, and an air inlet septum, through which pressurized air enters from the pump and controller unit, the air inlet septum sealing the vaginal interface element when no air is introduced therethrough.

BRIEF DESCRIPTION OF THE DRAWINGS

The present invention will be understood and appreciated more fully from the following detailed description, taken in conjunction with the drawings in which:

FIGS. 1A and 1B are simplified pictorial illustrations of an air speculum, in accordance with a non-limiting embodiment of the present invention, without a flexible vaginal interface element;

FIG. 1C is a simplified sectional illustration of the air speculum, constructed and operative in accordance with a non-limiting embodiment of the present invention, showing a flexible vaginal interface element that includes an air inlet, a pressure relief exit port, a tool channel and a tool channel plug;

DETAILED DESCRIPTION

Figures 1D, 2:
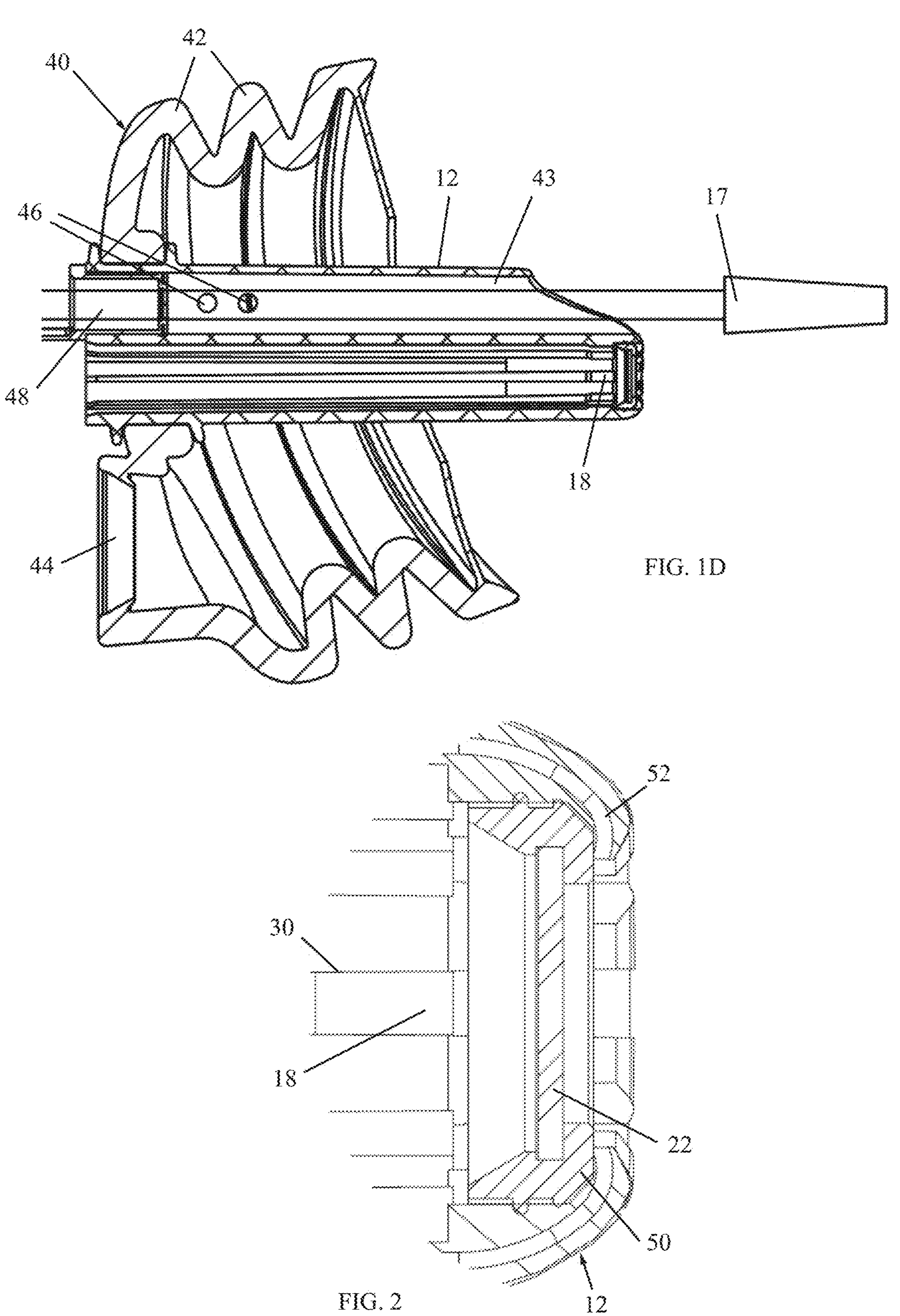
FIG. 1D is an enlarged illustration of the portion with the flexible vaginal interface element.
FIG. 2 is a simplified, enlarged sectional illustration of the distal end of the air speculum, showing a window and window seal, which are proximal to the distal face of the speculum, and proximal to the air outlet.

Reference is now made to FIGS. 1A and 1B, which illustrate an air speculum 10, constructed and operative in accordance with a non-limiting embodiment of the present invention. Speculum 10 may be similar to the speculum of PCT Patent Application PCT/IB2021/060539, but the invention is not limited to this speculum.

Speculum 10 includes a speculum sheath or shaft 12, which may be disposable, which couples with a light source 14, mounted on a handle 16. A viewing device (camera) 18 is arranged to pass into speculum sheath 12.

The speculum sheath 12 may be made of a medically-safe, rigid or flexible plastic (preferably transparent) and may be formed with several lumens. For example, one or more fluid flow lumens 20 (four are shown in the illustrated embodiment of FIG. 1B, but the invention is not limited to this number) may be in fluid communication via fluid connectors and tubing (not shown) with a pump and controller unit 24 (shown in FIGS. 3 and 4), for introducing pressurized air or other fluids into the vagina. Accordingly, there may be a pressure sensor lumen 20 in fluid communication with pump and controller unit 24 for measuring fluid pressure in the vagina.

As seen in FIG. 2, an imaging lumen 30 may be provided for placing therein viewing device 18. The light source 14 may be coupled to imaging lumen 30. The imaging lumen 30 may be closed at its distal end with an optically clear lens or window 22 to prevent any contact of tissues or fluids with viewing device 18 and avoid the need to sterilize viewing device 18.

The viewing device 18 may be, without limitation, a small diameter tube camera (1.6 mm) with a very wide lens (120°), good resolution and USB connection. The light source 14 may be one or more LEDs located on the handle 16. With light guides (e.g., optical fibers), the light is directed to the distal end of the device to illuminate the vaginal channel. With a wide lens and appropriate lighting, the user sees a well-illuminated picture of the vagina channel, and may move the device back and forth for viewing desired areas.

The light source 14 may be LEDs of different colors, such as but not limited to, red light for imaging deep veins or suspected lesions in tissues deep below the skin, green light for imaging suspected lesions on or close to the skin, white light and many others.

As seen in FIGS. 1A and 1B, the viewing device 18 may be positioned at the center of speculum sheath 12 and the ultrasonic transducer 34 may be positioned radially offset from the center of speculum sheath 12. Other lumens may be provided as working channels for passing therethrough tools, such as cutting tools, drug delivery tools, grasping tools, Pap smear test stick (denoted by numeral 17 in FIG. 1C), etc.

Figures 3, 4:
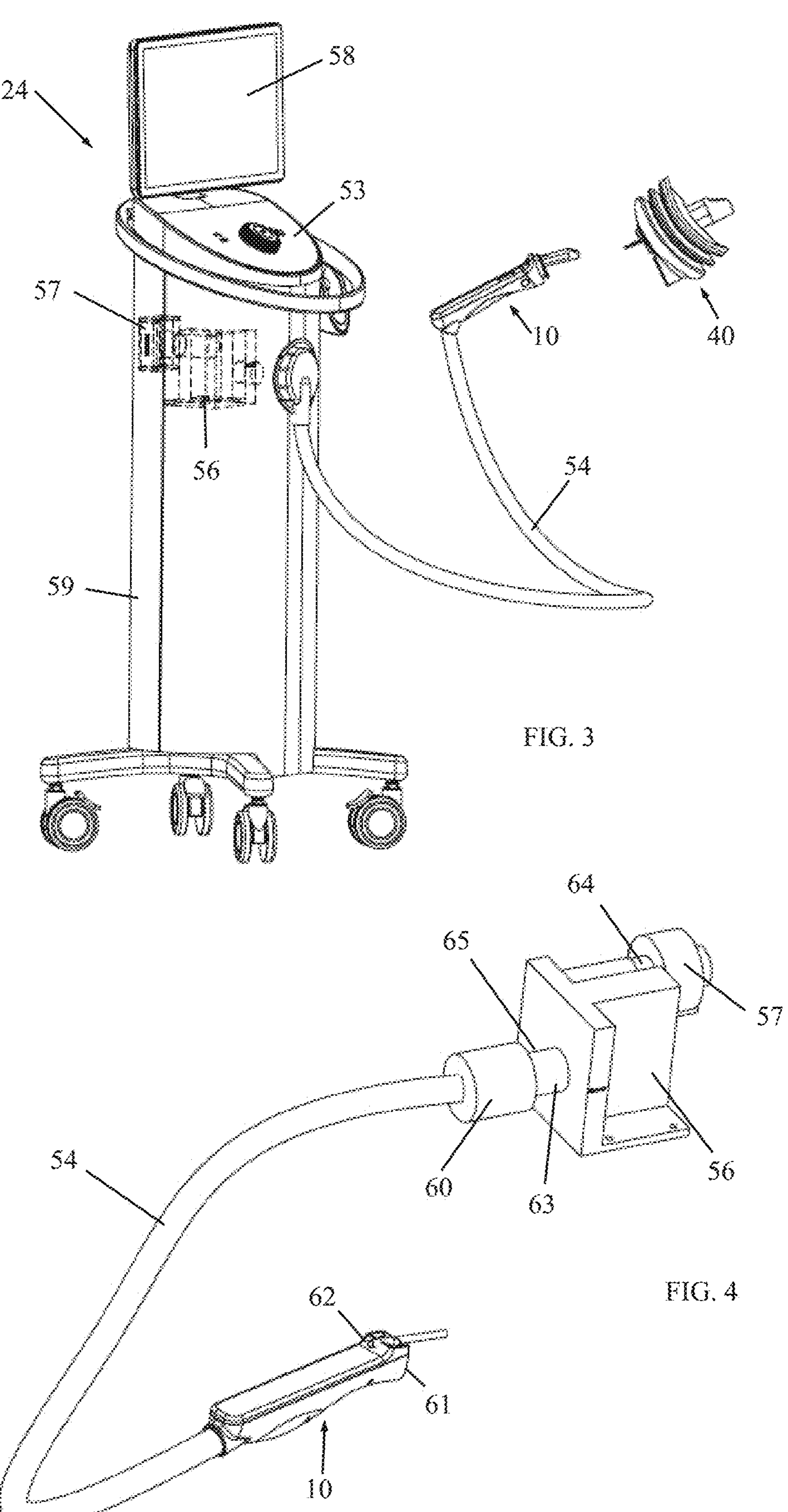
FIG. 3 is a simplified pictorial illustration of the air speculum coupled to a source of forced (compressed air) and to a processor and display, in accordance with a non-limiting embodiment of the present invention.
FIG. 4 is a simplified pictorial illustration of the compressed air source and connections to the applicator to which the air speculum is coupled.

Reference is now made to FIGS. 1C and 1D. The air speculum includes a vaginal interface element 40, which may include a soft, flexible cup with folds 42, shaped as a bellows, for example. The vaginal interface element 40 may include an air inlet septum 44, through which pressurized air can enter from pump and controller unit 24 (FIGS. 1A and 3). The air inlet septum 44 seals vaginal interface element 40 when no air is introduced through it. The air inlet septum 44 may be offset from the longitudinal central axis of vaginal interface element 40. Due to the presence of air inlet septum 44, the folds 42 may be asymmetric with respect to the longitudinal central axis of vaginal interface element 40; as seen, the folds 42 may be more compressed on one side of the longitudinal central axis as opposed to the opposite side. The folds 42 may be slanted (not perpendicular) with respect to the longitudinal central axis of vaginal interface element 40.

The vaginal interface element 40 may include one or more pressure relief exit ports 46. The purpose of ports 46 is as follows. When vaginal interface element 40 is pressed against the labia minora and/or labia majora of the vagina and pressurized air is introduced to inflate the vaginal canal, the pressure in the inflated vagina up to the cervix is about equal to the pressure in the inner volume of vaginal interface element 40. This pressure is greater than the external atmospheric pressure. When vaginal interface element 40 is moved away from the labia minora and/or labia majora of the vagina, unwanted air flow sounds may be caused. The pressure relief exit ports 46 prevent such unwanted sounds by venting some of the pressurized air.

FIG. 1C shows Pap smear test stick or other tool 17 passing through a tool channel (lumen) 43 of air speculum 10 and a tool channel plug 48 that seals the passage of the tool 17 through vaginal interface element 40. FIG. 1C shows tool 17 in solid lines after it has been passed distally through shaft 12 and the proximal positions is shown in broken lines.

Reference is now made to FIG. 2. The distal end of the speculum sheath 12 may include window 22 which is sealed by a window seal 50. An air outlet 52 may be provided through which some of the pressurized air flows distal to window 22. Accordingly, window 22 and seal 50 may be proximal to the distal end of speculum sheath 12 and proximal to the air outlet 52. The air exiting air outlet 52 may be used to prevent debris from forming or sticking on the distal end of shaft 12 and to prevent any humidity or fogging that could impair the camera from capturing images.

Reference is now made to FIG. 3. The air speculum 10 may be coupled by a tube 54 to pump and controller unit 24, which may include a source of forced (compressed) air 56, air filter 57 and display 58, mounted on a cart 59. A processor 53 may process any information sensed by the system and input into the system.

Reference is now made to FIG. 4. Tube 54 may be coupled to forced air source 56 by a connector 60. Pressure sensors 61, 62 (e.g., for measuring pressure inside and outside the vaginal interface element, such as pressure sensor lumen 20 of FIG. 1B), 63, 64 and 65 (e.g., for measuring pressure before and after the forced air source 56), may be in feedback communication with processor 53 (FIG. 4) to monitor the air pressure used in the system to ensure safety and efficacy of the system. Processor 53 may calculate air flow amount and rate from the air pressure sensed by the pressure sensors.

The device may be, without limitation, approximately 6 mm in diameter. Inflation fluid may be used to inflate the vaginal canal up to 20 mmHg, without limitation. The inflation fluid may be air, $CO_2$ or nitrogen, for example. The pressure sensors may be used to sense the real-time pressure in the vaginal tunnel to avoid pressure drops, and also may be used to as a pressure relief valve for safety. The pressure may be sensed by the control unit using PID (proportional integral derivative) control that operates in a control loop feedback for optimal safety and efficiency.

Figure 5:
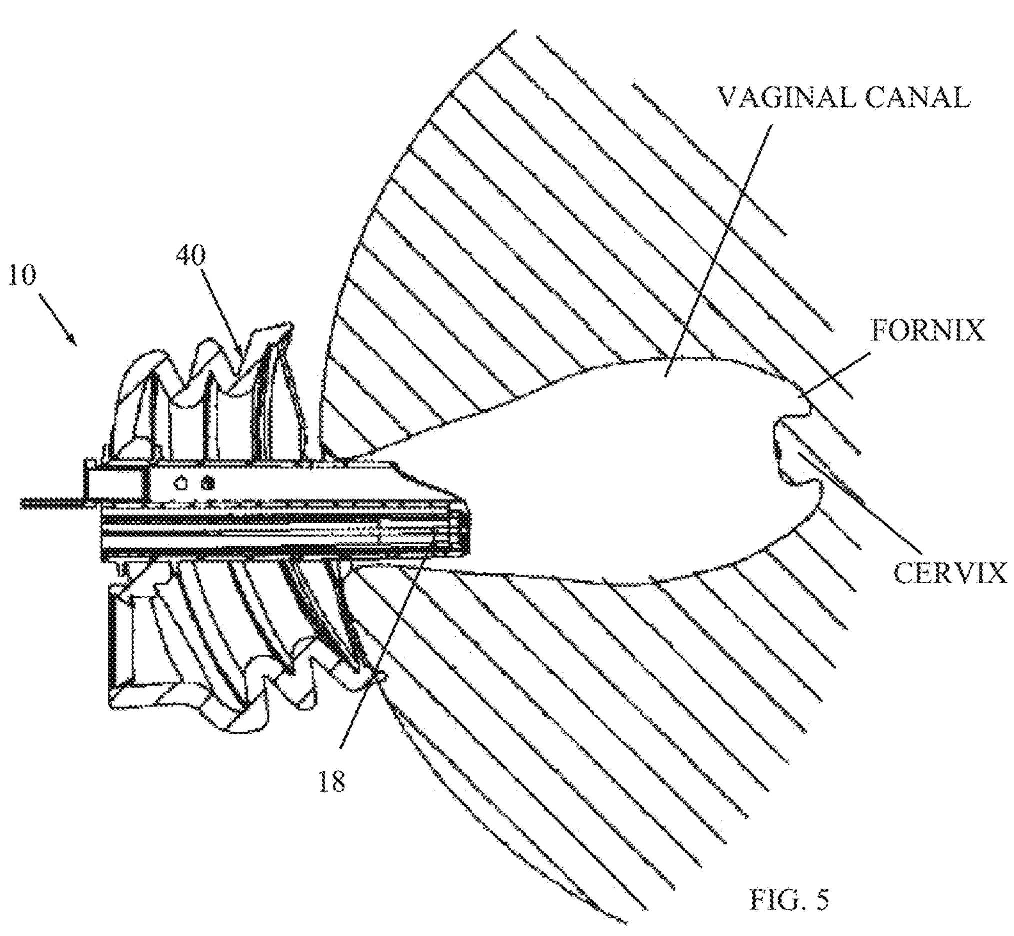
FIG. 5 is a simplified illustration of the anatomy after inflation by means of the air speculum.

Reference is now made to FIG. 5, which illustrates the anatomy after inflation by means of the air speculum 10. The cervix is now less tilted or not tilted at all with respect to the vagina and the fornix has flattened out. This greatly increases the visibility of the cervix and its accessibility for introducing instruments or substances.

Figure 6:
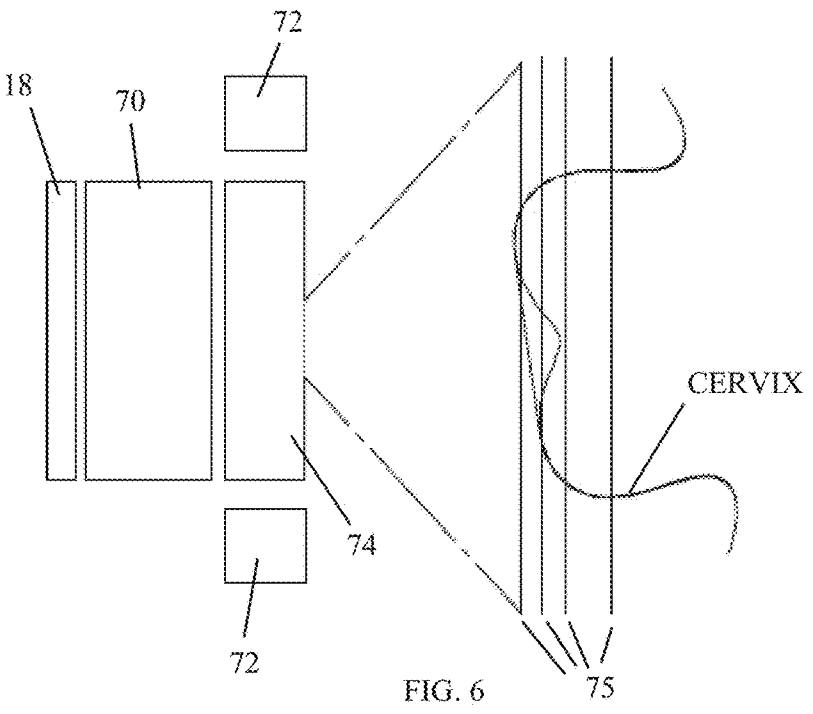
FIG. 6 is a simplified illustration of the image capturing optics of the system, which captures images at different focal planes in the vagina or cervix, in accordance with a non-limiting embodiment of the present invention.
Figures 7, 8:
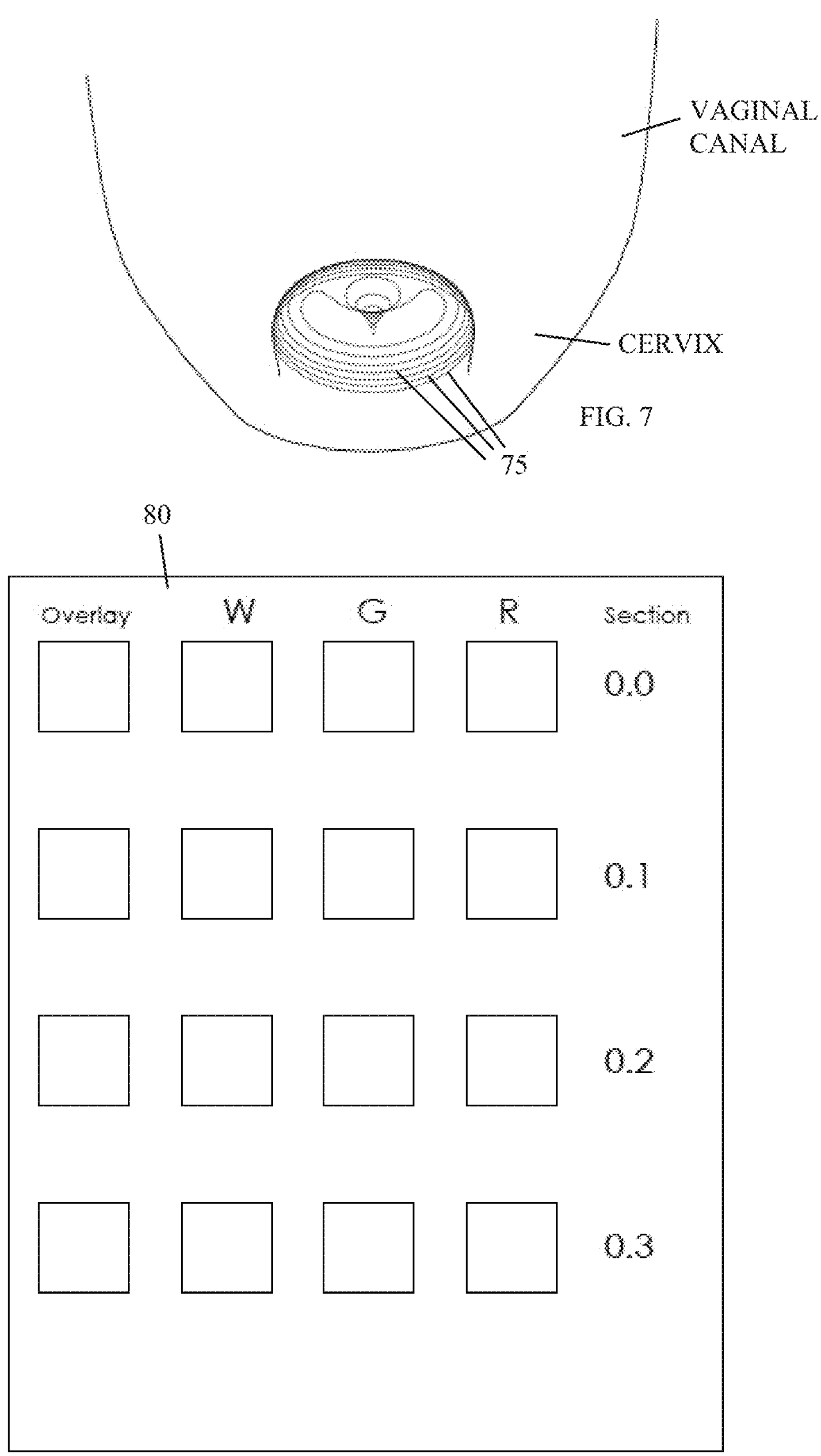
FIG. 7 is a simplified illustration of the different focal planes in the vagina or cervix.
FIG. 8 is an illustration of a display of the different focal planes imaged by the system.

Reference is now made to FIG. 6. The image capturing optics of the system may include limitation, camera 18 (e.g., a CMOS camera), an auto-focus module 70, LED 72 and optics 74 (e.g., magnifying lenses or other lenses). The image capturing optics of the system may capture images at different focal planes (indicated by section lines 75) in the vagina or cervix. FIG. 7 illustrates the different focal planes 75 in the vagina or cervix.

FIG. 8 illustrates a non-limiting exemplary display 80 of the different focal planes imaged by the system.

What is claimed is:

1. A speculum comprising:

a speculum sheath formed with one or more fluid flow lumens in fluid communication with a pump and controller unit for introducing pressurized fluid into a vagina, a pressure sensor lumen in fluid communication with said pump and controller unit for measuring fluid pressure in the vagina, and a viewing lumen in which is disposed a viewing device; and a vaginal interface element that comprises flexible folds and is configured for pressing and sealing against labia minora and/or labia majora of the vagina, said flexible folds being compressible in an axial direction along a longitudinal axis of said speculum sheath, wherein said flexible folds of said vaginal interface element comprise one or more pressure relief exit ports, wherein said vaginal interface element comprises an air inlet septum, through which pressurized air enters from said pump and controller unit, and wherein said air inlet septum is offset from a longitudinal central axis of said vaginal interface element.

2. The speculum according to claim 1, wherein said folds are asymmetric with respect to the longitudinal central axis of said vaginal interface element.

3. The speculum according to claim 1, wherein said folds are not perpendicular with respect to the longitudinal central axis of said vaginal interface element.

4. The speculum according to claim 1, wherein a distal portion of said speculum sheath comprises a window, sealed by a window seal, and an air outlet through which pressurized air can flow distal to said window, and wherein said window and said window seal are proximal to the distal end of said speculum sheath and proximal to said air outlet.

5. The speculum according to claim 1, further comprising image capturing optics.

6. The speculum according to claim 5, wherein said image capturing optics comprises a camera, an auto-focus module, an LED and one or more lenses, said image capturing optics operative to capture images at different focal planes.

7. The speculum according to claim 5, wherein said image capturing optics is operative to capture images at different focal planes in the vagina or a cervix.

* * * * *